United States Patent [19]
Aggarwal

[11] Patent Number: 5,891,924
[45] Date of Patent: Apr. 6, 1999

[54] CURCUMIN (DIFERULOYLMETHANE) INHIBITION OF NFκB ACTIVATION

[75] Inventor: Bharat B. Aggarwal, Houston, Tex.

[73] Assignee: Research Development Foundation, Carson City, Nev.

[21] Appl. No.: 712,932

[22] Filed: Sep. 26, 1996

[51] Int. Cl.⁶ .................................................. A61K 31/12
[52] U.S. Cl. ............................................................ 514/679
[58] Field of Search ............................................... 514/679

[56] References Cited

U.S. PATENT DOCUMENTS 4,959,503  9/1990  Connor et al. ........................... 564/265
5,401,504  3/1995  Das et al. ............................... 424/195.1
5,583,242  12/1996  Schieven ................................... 556/44

*Primary Examiner*—Theodore J. Criares
*Attorney, Agent, or Firm*—Benjamin Aaron Adler; McGregor & Adler P.C.

[57] ABSTRACT

The present invention provides a method of inhibiting the activation of the NFκB transcription factor in an animal in need of such treatment comprising the step of administering to said animal a pharmacologically effective dose of curcumin. Also provided is a method of inhibiting the nuclear translocation of the p65 subunit of the NFκB transcription factor in a cell or in an animal in need of such treatment comprising the step of administering to said animal a pharmacologically effective dose of curcumin.

2 Claims, 8 Drawing Sheets

CURCUMIN (DIFERULOYLMETHANE) INHIBITION OF NFκB ACTIVATION

BACKGROUND OF THE INVENTION

1. Field of the Invention

The present invention relates generally to the fields of immunology and protein chemistry. More specifically, the present invention relates to the use of curcumin to inhibit activation of the transcription factor, NFκB

2. Description of the Related Art

Members of the transcription factor NF-κB family play a central role in various responses leading to host defense, activating a rapid progression of gene expression. These transcription factors are dimeric complexes composed of different members of the Rel/NF-κB family of polypeptides. This family is distinguished by the presence of a Rel homology domain of about 300 amino acids that displays a 35% to 61% identity between various family members (for references see 1). Although NF-κB is a ubiquitous transcription factor, it plays a critical role in the cells of the immune system, where it controls the expression of various cytokines and the major histocompatibility complex genes. The inappropriate regulation of NF-κB and its dependent genes have been associated with various pathological conditions including toxic/septic shock, graft vs host reaction, radiation damage, atherosclerosis, and cancer (1, 2). Thus, NF-κB is an important target for therapeutic intervention.

Unlike other transcription factors, the NF-κB proteins and other members of the Rel family reside in the cytoplasm in a n inactive state but upon activation, they are translocated to the nucleus. The nuclear translocation of Rel proteins is induced b y many agents, including inflammatory cytokines (e.g., tumor necrosis factor (TNF), lymphotoxin (LT), and interleukin (IL)-1), mitogens, bacterial products, protein synthesis inhibitors, oxidative stress ($H_2O_2$), ultraviolet light, and phorbol esters (3, 4). Upon activation of NF-κB, a large number of genes are induced including various inflammatory cytokines, adhesion molecules, and Rel proteins (for reviews 3 and 4).

Curcumin (diferuloylmethane) has been shown to block many reactions in which NF-κB plays a major role. This agent is a major active component of turmeric (*Curcuma longa*) and gives specific flavor and yellow color to curry. The compound has been shown to display anticarcinogenic properties in animals as indicated by its ability to inhibit both tumor initiation induced by benz (a) pyrene and 7,12 dimethylbenz (a) anthracene (5–8) and tumor promotion induced by phorbol esters (9,10), which are known to activate NF-κB. Curcumin has also been shown to inhibit type 1 human immunodeficiency virus long terminal repeat (HIV-LTR) directed gene expression and virus replication stimulated by TNF and phorbol ester (11), which likewise require NF-κB activation. The anti-inflammatory and antioxidant properties of curcumin have been well documented (12–14). How these inhibitory responses are modulated by curcumin is not understood.

The prior art is deficient in the lack of effective means of inhibiting the activation of the transcription factor, NFκB. The present invention fulfills this longstanding need and desire in the art.

SUMMARY OF THE INVENTION

When activated, NF-κB, a ubiquitous transcription factor, binds DNA as a heterodimeric complex composed of members of the Rel/NF-κB family of polypeptides. Because of its intimate involvement in host defense against disease, this transcription factor is an important target for therapeutic intervention. The present invention demonstrates that curcumin (diferuloylmethane), a known antiinflammatory and anticarcinogenic agent, is a potent inhibitor of NF-κB activation. Treatment of human myeloid ML-1a cells with TNF rapidly activated NF-κB, which consists of p50 and p65 subunits, and this activation was inhibited by curcumin. AP-1 binding factors were also found to be down-modulated by curcumin, whereas the Sp1 binding factor was unaffected.

Besides TNF, curcumin also blocked phorbol ester- and hydrogen peroxide-mediated activation of NF-κB. The TNF-dependent phosphorylation and degradation of IκBα was not observed in curcumin-treated cells; the translocation of p65 subunit to the nucleus was inhibited at the same time. The mechanism of action of curcumin was found to be different from that of protein tyrosine phosphatase inhibitors. The present invention indicates that curcumin inhibits NF-κB activation pathway at a step before IκBα phosphorylation but after the convergence of various stimuli.

The present invention shows that curcumin is a potent inhibitor of NF-κB activation induced by various agents. The results also indicate that curcumin inhibits at a step in the signal transduction cascade of NF-κB activation that occurs before IκBα phosphorylation but after the point at which various signals transduced by different stimuli converge. The present invention shows that curcumin should be able to modulate NF-κB-dependent pathological conditions.

In one embodiment of the present invention, there is provided a method of inhibiting the activation of the NF-κB transcription factor in an animal in need of such treatment comprising the step of administering to said animal a pharmacologically effective dose of curcumin.

In another embodiment of the present invention, there is provided a method of inhibiting the nuclear translocation of the p65 subunit of the NFκB transcription factor in a cell or in an animal in need of such treatment comprising the step of administering to said animal a pharmacologically effective dose of curcumin.

In yet another embodiment of the present invention, there is provided a method of inhibiting the phosphorylation and degradation of IκBα protein in a cell or in an animal in need of such treatment comprising the step of administering to said animal a pharmacologically effective dose of curcumin.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

(FIG. 1a) ML-1a cells ($2 \times 10^6$/ml) were pre-incubated at 37° C. for 60 minutes with different concentrations (2 to 60 μM) of curcumin followed by 30 minutes incubation with 0.1 nM TNF. (FIG.

1b) ML-1a cells ($2\times10^6$/ml) were preincubated at 37° C. with 20 μM curcumin for different times and then measured NF-κB activation at 37° C. for 30 minutes either with or without 0.1 nM TNF. (−) indicates time curcumin was present before the addition of TNF, (0) indicates co-incubation with TNF and (+) indicates time curcumin was added after TNF. For FIG. 1C, ML-1a cells ($2\times10^6$/ml) were incubated at 37° C. with 50 μM curcumin for 60 minutes followed by treatment with 10 nM TNF for different times. After these treatments nuclear extracts were prepared and then assayed for NF-κB as described below. The arbitrary units represent the relative amounts of the radioactivity present in respective bands.

FIG. 2 shows the supershift analysis and specificity of the effect of curcumin on the NF-κB activation. For FIG. 2a, nuclear extracts (NE) were prepared from untreated or TNF (0.1 nM)-treated ML-1a cells ($2\times10^6$/ml), incubated for 30 minutes with antibodies and then assayed for NF-κB as described below. For FIG. 2b, nuclear extracts prepared from TNF pre-treated cells were incubated with different concentrations of curcumin for 15 minutes and then analyzed for NF-κB by EMSA.

FIG. 6 shows the effect of curcumin on TNF-induced phosphorylation and degradation of IκBα and on level of p65 in cytoplasm and nucleus. ML-1a ($2\times10^6$/ml) pretreated (for 60 minutes at 37° C.) with or without curcumin (50 μM) were incubated for different times with TNF (0.1 nM), and then assayed for IκBα (FIG. 6A) and for p65 (FIG. 6B) in cytosolic fractions by western blot analysis as described below. ML-1a ($2\times10^6$/ml) pretreated (for 60 minutes at 37° C.) with curcumin were incubated with TNF (0.1 nM) for 30 minutes. Nuclear and cytoplasmic extracts were assayed by western blot analysis for p65. The arbitary units represent the relative amounts of the respective proteins as described below.

DETAILED DESCRIPTION OF THE INVENTION

In the present invention, the following abbreviations may be used: TNF, tumor necrosis factor; PTPase, protein tyrosine phosphatase; PTK, protein tyrosine kinase; PPase, protein phosphatase; PAO, phenylarsine oxide; DTT, dithiothreitol; DMP, 2,3-dimercaptopropanol; FBS, fetal bovine serum; HIV-LTR, human immunodeficiency virus- 1 long terminal repeat.

The present invention is directed to a method of inhibiting the activation of the NFκB transcription factor in an animal in need of such treatment comprising the step of administering to said animal a pharmacologically effective dose of curcumin. Most preferably, the animal is a human. Preferably, the human has a pathophysiological state selected from the group consisting of toxic/septic shock, graft vs host reaction, radiation damage, atherosclerosis, and cancer. Although the curcumin may be given in any dose which suitably inhibits the activation of the NF-κB transcription factor, the curcumin is preferably administered in a dose of from about 1 mg/kg to about 100 mg/kg.

The present invention is also directed to a method of inhibiting the nuclear translocation of the p65 subunit of the NFκB transcription factor in a cell in an animal in need of such treatment comprising the step of administering to said animal a pharmacologically effective dose of curcumin. For this method, the animal is preferably a human. Preferably, the human has a pathophysiological state selected from the group consisting of toxic/septic shock, graft vs host reaction, radiation damage, atherosclerosis, AIDS, inflammation and cancer. Although the curcumin may be given in any dose which suitably inhibits th e activation of the NF-κB transcription factor, the curcumin is preferably administered in a dose of from about 1 mg/kg to about 100 mg/kg.

The present invention also provides a method of inhibiting the phosphorylation and degradation of IκBα protein in a cell or in an animal in need of such treatment comprising the step of administering to said animal a pharmacologically effective dose of curcumin. Preferably, the animal is a human. A method of inhibiting the phosphorylation and degradation of IκBα protein in a cell or in an animal is relevant where the human has a pathophysiological state selected from the group consisting of toxic/septic shock, graft vs host reaction, radiation damage, atherosclerosis, and cancer. Preferably, the curcumin is administered in a dose of from about 1 mg/kg to about 100 mg/kg.

The following examples are given for the purpose of illustrating various embodiments of the invention and are not meant to limit the present invention in any fashion.

EXAMPLE 1

Materials:

Penicillin, streptomycin, RPMI 1640 medium, and fetal calf serum were obtained from GIBCO (Grand Island, N.Y.). Curcumin, glycine, NaCl, and bovine serum albumin were obtained from Sigma Chemical Co. (St. Louis, Mo.), and phenylarsine oxide from Aldrich Chemicals (Milwaukee, Wis.). Bacteria-derived recombinant human TNF, purified to homogeneity with a specific activity of $5\times10^7$ units/mg, was kindly provided by Genentech, Inc. (South San Francisco, Calif.). Antibody against IκBα, cyclin D1 and NF-κB subunits p50 and p65 and double stranded oligonucleotides having AP-1 and SP1 consensus sequences were obtained from Santa Cruz Biotechnology (Santa Cruz, Calif.).

EXAMPLE 2

Cell lines:

The cell line employed was ML-1a, a human myelomonoblastic leukemia cell line provided by Dr. Ken Takeda of Showa University, Japan. Cells were routinely grown in RPMI 1640 medium supplemented with glutamine (2 mM), gentamicin (50 mg/ml), and fetal bovine serum (FBS) (10%). The cells were seeded at a density of $1\times10^5$ cells/ml in T25 flasks (Falcon 3013, Becton Dickinson Labware, Lincoln Park, N.J.) containing 10 ml of medium and grown at 37° C. in an atmosphere of 95% air and 5% $CO_2$. Cell cultures were split every 3 or 4 days. Occasionally, cells were tested for mycoplasma contamination using the DNA-based assay kit purchased from Gen-Probe (San Diego, Calif.).

EXAMPLE 3
Electrophoretic Mobility Shift Assays:

ML-1a cells ($2\times10^6$ cells/ml) were treated separately with different concentrations of an activator at 37° C. Nuclear extracts were then prepared according to Schreiber et al. (15). Briefly, $2\times10^6$ cells were washed with cold phosphate-buffered saline (PBS) and suspended in 0.4 ml of lysis buffer (10 mM HEPES pH 7.9, 10 mM KCl, 0.1 mM EDTA, 0.1 mM EGTA, 1 mM DTT, 0.5 mM PMSF, 2.0 mg/ml leupeptin, 2.0 mg/ml aprotinin, and 0.5 mg/ml benzamidine). The cells were allowed to swell on ice for 15 minutes, after which 12.5 ml of 10% NP-40 was added. The tube was then vigorously mixed on a vortex machine for 10 seconds, and the homogenate was centrifuged for 30 seconds in a microfuge. The nuclear pellet was resuspended in 25 µl ice-cold nuclear extraction buffer (20 mM HEPES pH 7.9, 0.4 M NaCl, 1 mM EDTA, 1 mM EGTA, 1 mM DTT, 1 mM PMSF, 2.0 mg/ml leupeptin, 2.0 mg/ml aprotinin, and 0.5 mg/ml benzamidine), and the tube was incubated on ice for 30 minutes with intermittent mixing. The tube was then centrifuged for 5 minutes in a microfuge at 4° C., and the supernatant (nuclear extract) was either used immediately or stored at −70° C. for later use. The protein content was measured by the method of Bradford (16).

Electrophoretic mobility shift assays (EMSA) were performed by incubating 4 mg of nuclear extract (NE), with 16 fmoles of $^{32}p$ end-labeled 45-mer double-stranded NF-κB oligonucleotide from the HIV-LTR, 5'-TTGTTACAAGGGACTTTCCGCTG GGGACTTTCCAGGGAGGCGTGG-3', (17) for 15 minutes at 37° C. The incubation mixture included 2–3 mg of poly (dI-dC) in a binding buffer (25 mM HEPES pH 7.9, 0.5 mM EDTA, 0.5 mM DTT, 1% NP-40, 5% glycerol, and 50 mM NaCl) (18, 19). The DNA-protein complex formed was separated from free oligonucleotide on 4.5% native polyacrylamide gel using buffer containing 50 mM Tris, 200 mM glycine pH 8.5, and 1 mM EDTA (20), and then the gel was dried. A double-stranded mutated oligonucleotide, 5'TTGTTACAACTCACTTTCCGCTGCCACTTTCCA-GGGAGGCGTGG-3', was used to examine the specificity of binding of NF-κB to the DNA. The specificity of binding was also examined by competition with the unlabeled oligonucleotide.

For supershift assays, nuclear extracts prepared from TNF treated cells were incubated with the antibodies against either p50 or p65 subunits of NF-κB for 30 minutes at room temperature before the complex was analyzed by EMSA (21). Antibodies against cyclin D1 and preimmune serum were included as negative controls.

The EMSAs for AP-1 and Sp1 were performed as described for NF-κB using $^{32}p$ end-labeled double-stranded oligonucleotides. Specificity of binding was determined routinely by using an excess of unlabeled oligonucleotide for competition as described earlier (21). Visualization and quantitation of radioactive bands was carried out by a phosphorimager (Molecular Dynamics, Sunnyvale, Calif.) using 'Image-quant' software.

EXAMPLE 4
Electrophoretic Mobility Shift Assays:

ML-1a cells ($2\times10^6$ cells/ml) were treated separately with different concentrations of an activator at 37° C. Nuclear extracts were then prepared according to Schreiber et al. (15). Briefly, $2\times10^6$ cells were washed with cold phosphate-buffered saline (PBS) and suspended in 0.4 ml of lysis buffer (10 mM HEPES pH 7.9, 10 mM KCl, 0.1 mM EDTA, 0.1 mM EGTA, 1 mM DTT, 0.5 mM PMSF, 2.0 mg/ml leupeptin, 2.0 mg/ml aprotinin, and 0.5 mg/ml benzamidine). The cells were allowed to swell on ice for 15 minutes, after which 12.5 ml of 10% NP-40 was added. The tube was then vigorously mixed on a vortex machine for 10 seconds, and the homogenate was centrifuged for 30 seconds in a microfuge. The nuclear pellet was resuspended in 25 µl ice-cold nuclear extraction buffer (20 mM HEPES pH 7.9, 0.4 M NaCl, 1 mM EDTA, 1 mM EGTA, 1 mM DTT, 1 mM PMSF, 2.0 mg/ml leupeptin, 2.0 mg/ml aprotinin, and 0.5 mg/ml benzamidine), and the tube was incubated on ice for 30 minutes with intermittent mixing. The tube was then centrifuged for 5 minutes in a microfuge at 4° C., and the supernatant (nuclear extract) was either used immediately or stored at −70° C. for later use. The protein content was measured by the method of Bradford (16).

EXAMPLE 5
Western Blotting for IκBα and p65:

After the NF-κB activation reaction described above, postnuclear extracts were resolved on 10% SDS-polyacrylamide gels for IκBα. To determine p65 levels, nuclear and post nuclear (cytoplasmic) extracts were resolved on 8% SDS-polyacrylamide gels. After the gels, the proteins were electrotransferred to nitrocellulose filters, probed with a rabbit polyclonal antibody against IκBa or against p65, and detected by chemiluminescence (ECL-Amersham) (22). The bands obtained were quantitated using Personal Densitometer Scan v1.30 using Image Quanta software version 3.3 (Molecular Dynamics, Sunnyvale, Calif.).

EXAMPLE 6
Results

The present invention demonstrated the effect of curcumin on the activation of transcription factor NF-κB. Human ML-1a cells were used for these studies because their response to NF-κB activation by various stimuli has been well characterized (21–23). The time of incubation and the concentration of the drugs used in the studies had no effect on the cell viability (data not shown).

EXAMPLE 6
Curcumin inhibits TNF-Dependent NF-κB activation

Figure 1A:
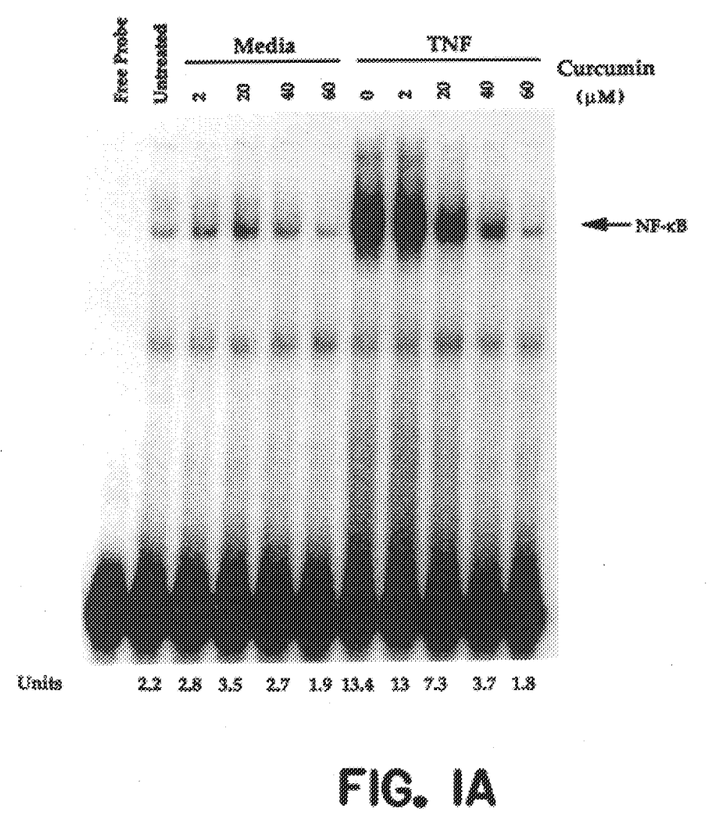
FIG. 1 shows the dose response and kinetics of inhibition of TNF-dependent NF-κB by curcumin.
Figure 1B:
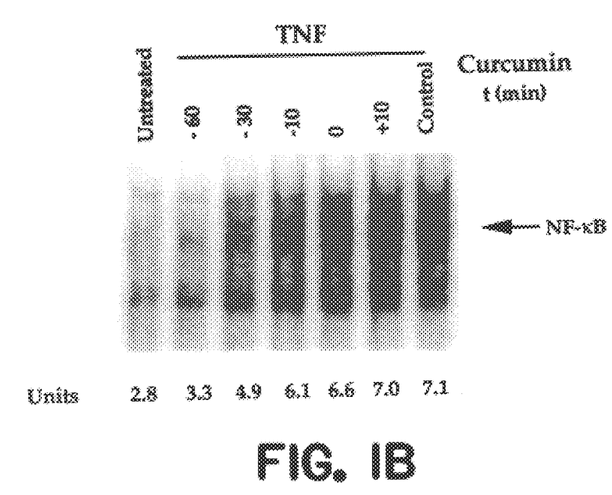

ML-1a cells were preincubated for 1 hour with different concentrations of curcumin followed by treatment with TNF (0.1 nM) for 30 minutes at 37° C. They were then examined for NF-κB activation by electrophoretic mobility shift assay. The results in FIG. 1a indicate that 40–60 µM curcumin inhibited most of the TNF response. Curcumin by itself did not activate NF-κB. The kinetics of inhibition were shown next, incubating the cells with curcumin either for 60, 30 and 10 minutes prior to the addition of TNF, at the same time as the addition of TNF, or 10 minutes after the addition of TNF. The cells were treated with TNF for 30 minutes. TNF response was inhibited only when cells were pretreated with curcumin (FIG. 1b). Cotreatment of cells with TNF and curcumin was not effective.

Figure 1C:
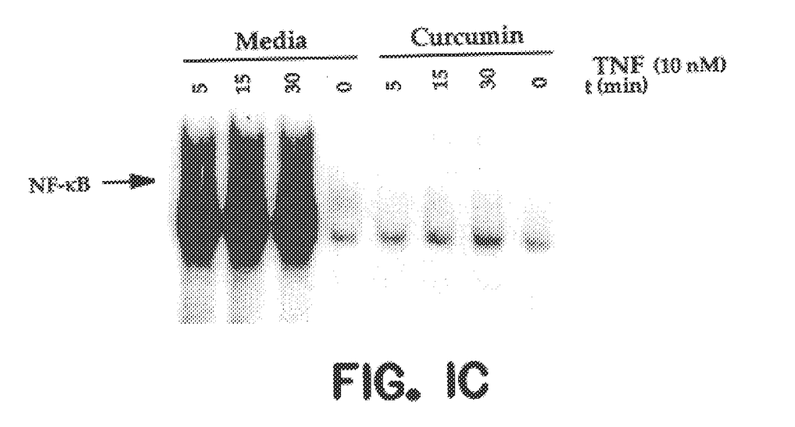

A high concentration of TNF (10 nM) can activate NF-κB within 5 minutes and this induction is higher in its intensity than that obtained with cells using 100-fold lower concentration of TNF for longer time (23). To determine the effect of curcumin on NF-κB activation at higher TNF concentration and its effect on kinetics of TNF-mediated activation of NF-κB, curcumin-pretreated cells were exposed to 10 nM TNF for various times (FIG. 1c). The induction of NF-κB by 10 nM TNF was very high and occurred within 5 minutes. Curcumin could completely inhibit the activation of NF-κB induced by 10 nM as efficiently as it did with 0.1 nM TNF. Thus, curcumin is a very potent inhibitor of NF-κB activation.

Figure 2A:
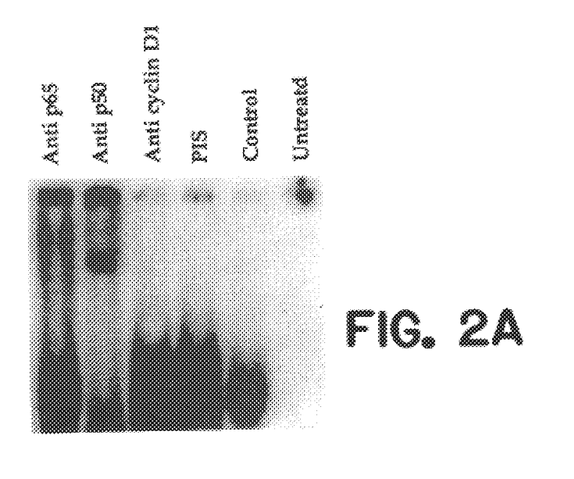

To show that the retarded band observed by EMSA in TNF-treated cells was indeed NF-κB, the nuclear extracts were incubated with antibody to either p50 (NF-κB1) or p65 (Rel A) subunits and then carried out EMSA. The results from this experiment (FIG. 2a) show that antibodies to either subunit of NF-κB shifted the band to higher molecular weight, thus suggesting that the TNF-activated complex consisted of p50 and p65 subunits. Neither preimmune serum nor irrelevant antibody against cyclin D had any effect on the mobility of NF-κB.

Figure 2B:
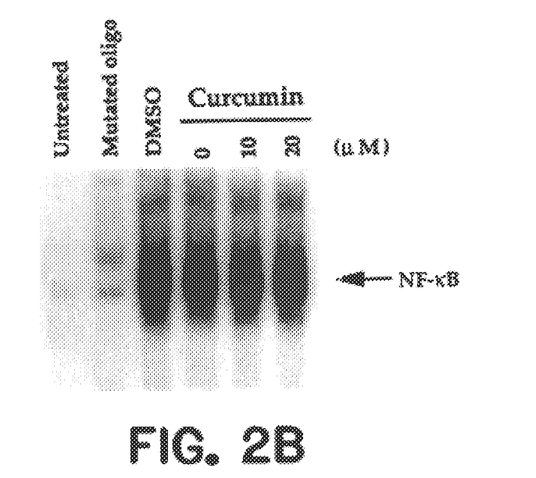

Both TPCK and herbimycin A have been shown to interfere with the binding of NF-κB to the DNA (25, 52). To determine the effect of curcumin on the binding of NF-κB to the DNA, the nuclear extracts from TNF-pre-activated cells were incubated with curcumin and then EMSA was performed. The results of this experiment (FIG. 2b) show that curcumin did not modify the ability of NF-κB to bind to the DNA.

EXAMPLE 7

Figure 3:
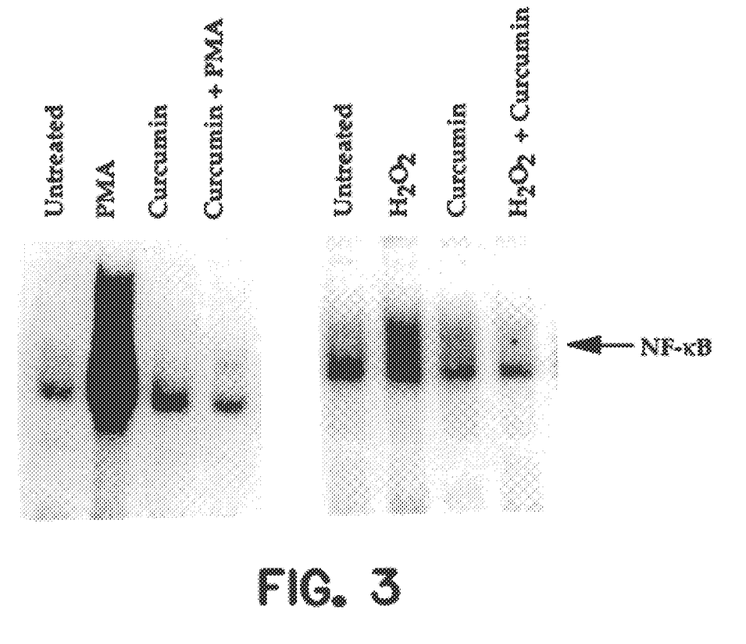
FIG. 3 shows the effect of Curcumin on PMA- and $H_2O_2$-mediated activation of NF-κB. ML-1a cells ($2\times10^6$/ml) were preincubated for 60 minutes at 37° C. with curcumin (50 μM) followed by PMA (25 ng/ml) or $H_2O_2$ (0.5 mM) or indicated combinations for 30 minutes and then tested for NF-κB activation as described below.

Curcumin Also Blocks Phorbol Ester- and Hydrogen Peroxide-Mediated Activation of NF-κB Besides TNF, NF-κB activation is also induced by phorbol ester (PMA), and hydrogen peroxide (49). However the initial signal transduction pathway induced by these agents that leads to the NF-κB activation differs. Therefore, the effect of curcumin on activation of the transcription factor by these various agents was examined. The results shown in FIG. 3 indicate that curcumin completely blocked PMA and hydrogen peroxide-induced activation of NF-κB. Thus, curcumin is a general suppressor of NF-κB activation.

EXAMPLE 8

Figure 4:
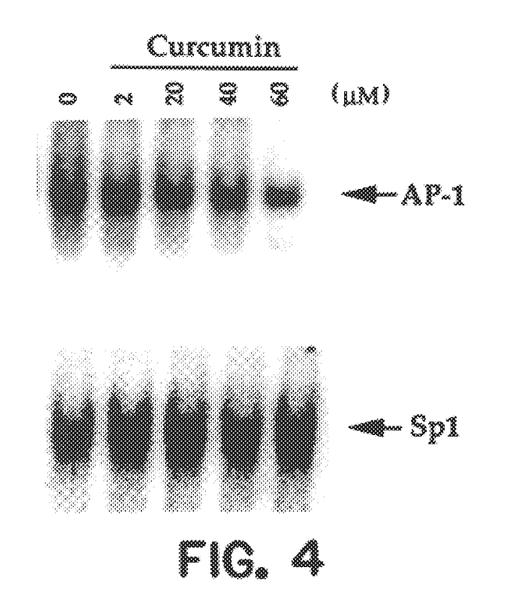
FIG. 4 shows the effect of curcumin on AP-1 and Sp1 transcription factors. Cells were treated with different concentrations of curcumin for 60 minutes at 37° C., and nuclear extracts were then prepared and used for EMSA of AP-1 and Sp1 transcription factors as described below.

Curcumin down-modulates AP-1 but not Sp1 transcription factors:

Whether curcumin specifically blocks the activation of NF-κB or also affects other transcription factors was investigated. Curcumin had no effect on the Sp1 transcription factor (FIG. 4); however, DNA binding of AP-1 transcription factors was found to be down-modulated. This result is in agreement with an earlier report which showed that curcumin not only inhibits the DNA-binding activity of c-Jun/AP-1 binding factors but also down-modulates the level of these factors (24).

EXAMPLE 9

Figure 5:
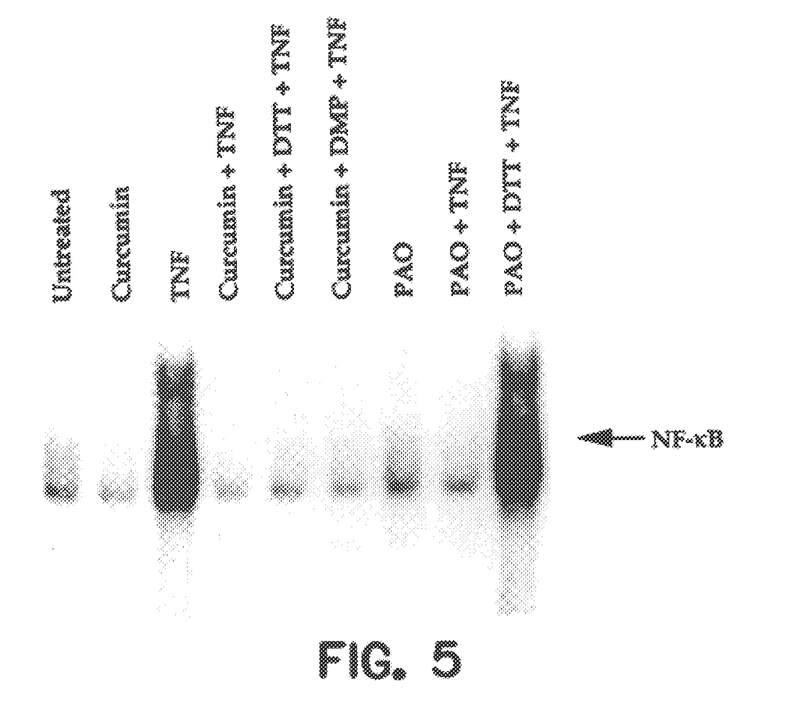
FIG. 5 shows the effect of DTT and DMP on the Curcumin and PAO-induced inhibition of NF-κB activation. ML-1a ($2\times10^6$/ml) were incubated at 37° C. for 60 minutes with DTT (100 μM) or DMP (100 μM) in the presence of Curcumin (50 μM) or PAO (2.4 μM) or indicated combinations followed by 30 minutes incubation with 0.1 nM TNF and then assayed for NF-κB activation as described below.

Reducing Agents Do Not Reverse the Effect of Curcumin:

It has been shown that agents like TPCK that modify the sulfhydryl group in NF-κB inhibit its activation but this inhibition is prevented in the presence of DTT and DMP (25, 31). DTT and DMP can also reverse the inhibitory effect of phenylarsine oxide (PAO; a potent PTPase inhibitor) on NF-κB activation (21). To determine if the inhibitory effect of curcumin on NF-κB was reversed by these reducing agents, ML-1a cells were treated with curcumin in the presence and absence of either DTT or DMP and then examined for the activation of NF-κB by TNF. As shown in FIG. 5, DTT and DMP did not reverse the inhibition caused by curcumin but completely reversed the PAO-mediated inhibition. These results thus suggest that the mechanism of action of curcumin is different from that of PTPase inhibitors.

EXAMPLE 10

Figure 6A:
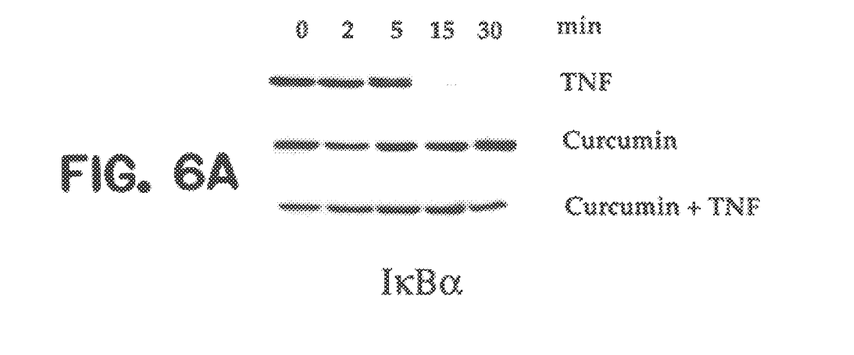

Curcumin inhibits TNF-dependent phosphorylation and degradation of IκBα and translocation of p65 subunit of NF-κB to the nucleus:

The translocation of NF-κB to the nucleus is preceded by the phosphorylation and proteolytic degradation of IκBα (26). To determine whether the inhibitory action of curcumin was due to its effect on IκBα degradation, the cytoplasmic levels of IκB protein were examined by western blot analysis. IκBa was phosphorylated within 5 minutes of TNF treatment of ML-1a cells and then disappeared within 15 minutes. However, curcumin abolished both the phosphorylation (as indicated by absence of the slow migrating band) and degradation of IκBα induced by TNF (FIG. 6A).

Figure 6B:
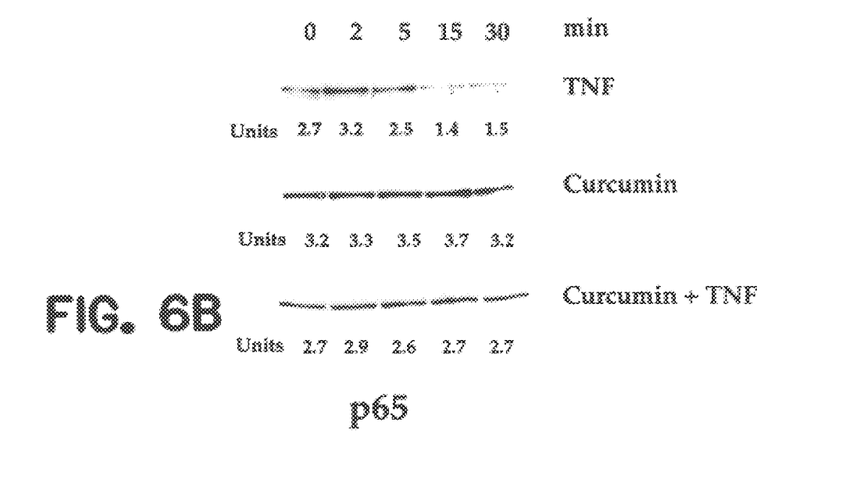
Figure 6C:
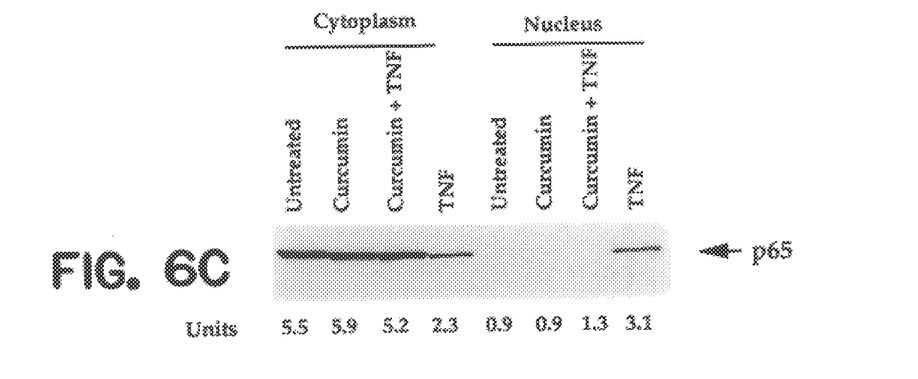
Figure 7:
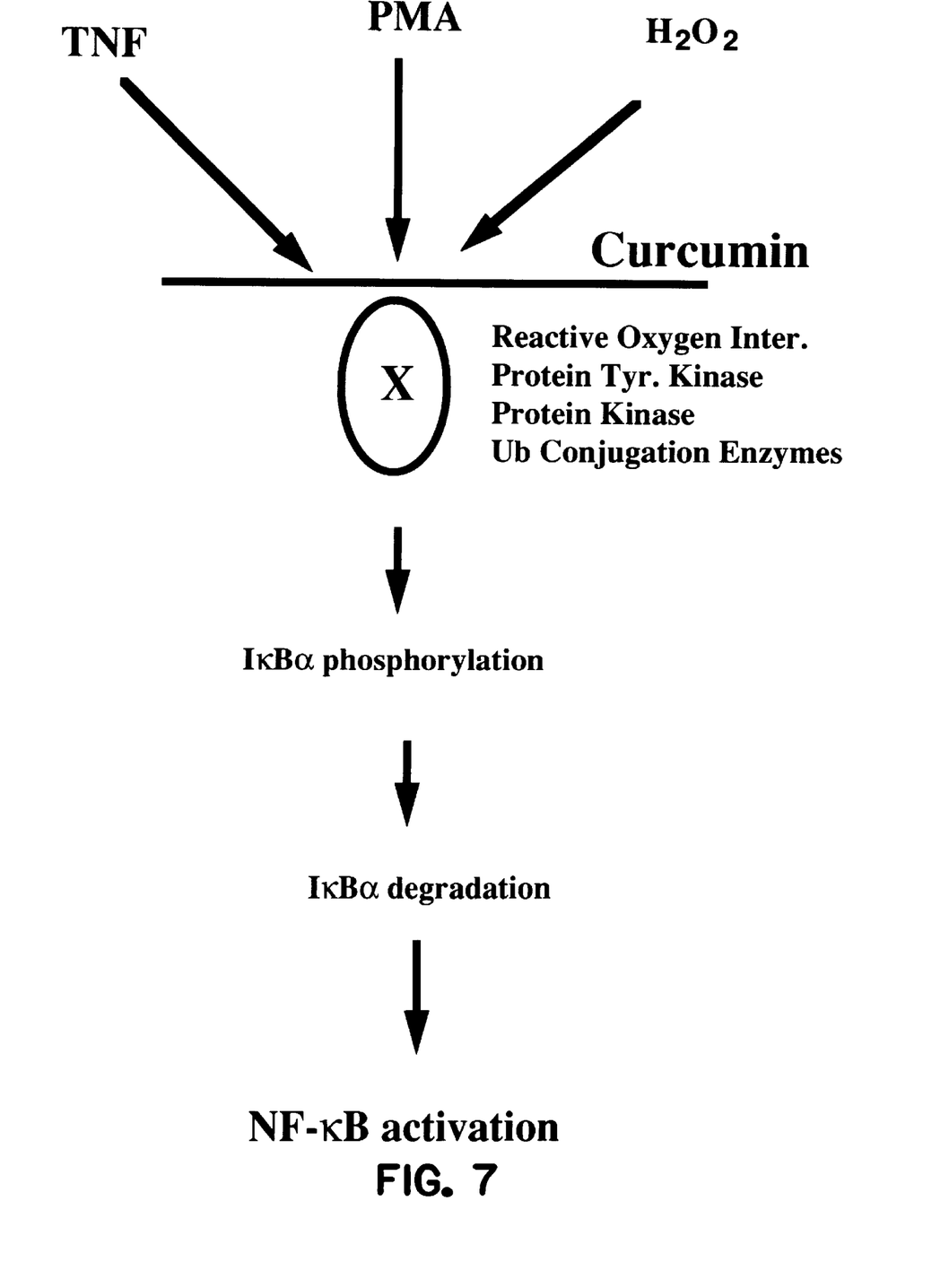
FIG. 7 shows the possible site of action of curcumin on TNF- PMA- and $H_2O_2$- induced NF-κB activation.

The level of p65 in the cytoplasm and in the nucleus was also measured. As expected upon TNF treatment, the level of p65 declined in the cytoplasm with a concurrent increase in the nucleus (FIGS. 6B and 6C). The treatment of cells with curcumin abolished the TNF-dependent change in the nuclear and cytoplasmic p65 levels. These results show that curcumin inhibits the TNF-induced translocation of p65 to the nucleus and this is consistent with the inhibition of TNF-dependent degrdation of IκBα by curcumin.

Curcumin is a pharmacologically safe compound with known anti-inflammatory, anticarcinogenic, and free radical scavenger properties (6, 10, 27–30). However, how curcumin carries out these functions is not very clear. NF-κB plays a pivotal role in cells of the immune system because it is rapidly activated by wide variety of pathogenic signals and functions as a potent and pleiotropic transcriptional activator. Intervention in NF-κB activation may be beneficial in suppressing toxic/septic shock, graft-vs-host reactions, acute inflammatory reactions, HIV replication, acute phase response and radiation damage.

The present invention demonstrates that curcumin completely blocked the TNF-dependent activation of NF-κB. The activation induced by various other agents including phorbol ester and $H_2O_2$ was also inhibited by curcumin. As has been shown with other inhibitors, the effect of curcumin was not due to the chemical modification of NF-κB proteins (25, 31, 52). The inhibition of NF-κB activation was accompanied by the inhibition of p65 translocation to the nucleus and of IκB degradation.

Identifying how curcumin blocks the activation of NF-κB requires an understanding of the mechanism by which various inducers activate this important transcription factor. The role of different TNF-activated signals including acidic and neutral sphingomyelinase-generated ceramides, proteases, serine/threonine protein kinase (PK), protein tyrosine kinase (PTK), protein tyrosine phosphatase (PTPase) and superoxide radicals in the activation of NF-κB have been implicated (1, 21, 22, 32–35). Whether these signals are generated by TNF sequentially or independently of each other, however, is not understood.

All three inducers of NF-κB used in these studies are known to produce reactive oxygen intermediates (ROI). Therefore, it is possible that the effect of curcumin is through quenching of ROI production. The inhibitors of mitochondrial electron transport have been shown to impair the TNF-induced activation of NF-κB (36), thus also suggesting the role of ROI. Several additional, indirect lines of evidence suggest a role for ROI as a common and critical denominator (40, 41), including evidence that cellular levels of ROI increase in response to TNF, IL-1, PMA, LPS, UV light, and gamma irradiation (for references see 1). But among the various ROI administered to cells in culture, only hydrogen peroxide was found to be an effective activator of NF-κB (42).

Curcumin may also block NF-κB activation by inhibiting a protein kinase. In vitro, curcumin has been shown to inhibit both serine/threonine PK and PTK (44). The PK needed for the activation of NF-κB has not, however, been identified. Although PMA is an activator of PkC, both TNF and $H_2O_2$ have been shown to activate both PkC and PTK. NF-κB activation by TNF and $H_2O_2$ has been shown to be blocked by inhibitors of both PKC and PTK (50). The role of a PTK has also been implicated in NF-κB activation by ultraviolet light, lipopolysaccharide, hypoxia, and v-src (37–40, 51). TNF-dependent activation of NF-κB is dependent on erbstatin-sensitive PTK (22). Studies of Schieven et al 1993 (43) showed that PTK inhibitors block gamma-irradiation-induced NF-κB activation, a stimulant thought to work through the immediate generation of ROI, which suggest that PTK activation may precede ROI generation. Thus there are different early events involved in activation of NF-κB but all of them may converge to phosphorylate the IκKBa which precedes its degradation and the subsequent translocation of p65 into the nucleus.

It has been shown that curcumin not only inhibits the DNA binding of c-jun/AP-1 transcription factor but it also down-modulates c-jun level by preventing its transcription (24). Curcumin did not inhibit the Sp1 transcription factor under the same conditions in which it inhibited NF-κB and AP-1 transcription factors. Curcumin has also been shown to inhibit TNF and phorbol ester-stimulated type 1 HIV-LTR-directed gene expression and virus replication (11), and this may be mediated through the inhibition of NF-κB. Recently it has been reported that curcumin can also inhibit nitric oxide synthase (45–47). These observations can be explained based on these results since the expression of this enzyme is NF-κB dependent. This is consistent with the observation that TPCK, a protease inhibitor that blocks NF-κB activation, also blocks the expression of nitric oxide synthase (48). TPCK, however, may exert its effect by a different mechanism than curcumin does. It has been shown that TPCK chemically modifies NF-κB, thus altering its release from IκBa (25). Curcumin, however, does not chemically modify the DNA binding properties of NF-κB.

Another level of modification that could prevent formation of p50/p65 heterodimer is down-modulation of the cytoplasmic pool of p65 subunit of NF-κB. The present invention, however, shows that p65 was not down-modulated by curcumin but its translocation to the nucleus was inhibited, most likely through inhibition of degradation of IκB.

The observation that TNF-induced phosphorylation and degradation of IκBα is abolished by curcumin indicate that the step in the signal transduction pathway of NF-κB activation inhibited by this agent is at or before the phosphorylation step of NF-κB (FIG. 8). That it can inhibit NF-κB activation by diverse agents indicates that this step is after or at the step where the diverse signals converge. Overall, because of its very low pharmacological toxicity and its ability to modulate activation of NF-κB by various agents, curcumin has a high potential for use in modulating expression of genes regulated by NF-κB.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The following references were cited herein:
1. Siebenlist, et al., (1994) Annu. Rev. Cell Biol, 10. 405–455.
2. Baeuerle, et al., (1994) Annu. Rev. Immunol. 12, 141–179.
3. Baeuerle, P. A.(1991) Biochem. Biophys Acta 1072, 63–80.
4. Grilli, M., et al., (1993) Int. Rev. Cytol. 143. 1–62.
5. Huang, et al., (1992) Carcinogenesis 13, 2183–2186.
6. Azuine, M. A. and Bhide, S. V. (1992) Nutr. Cancer 17, 77–83.
7. Azuine, M. A. and Bhide, S. V. (1992) Int. J. Cancer 51, 412–415.
8. Nagbhusan, et al., (1992) J. Am. Coll. Nutr. 11, 192–198.
9. Huang, et al., (1988) Cancer Res. 48, 5941–5946.
10. Conney, et al., (1991) Adv. Enzyme Regul. 31. 385–396.
11. Li, et al., (1993) Proc. Natl. Acad. Sci. U.S.A., 90, 1839–1842.
12. Ammon, et al., (1991) Planta. Med. 57, 1–7.
13. Satoskar, et al., (1986) Int. J. Clin. Pharmacol. Res. 24, 651–654.
14. Shankar, et al., (1980) Indian J. Expt. Biol. 18, 73–75.
15. Schreiber, et al., 1989. Nucleic Acids Res. 17: 6419.
16. Bradford, M. M. 1976. Anal. Biochem. 72: 248–254.
17. Nabel, G. and D. Baltimore. 1987. Nature 326: 711.
18. Collart, et al., 1990. Mol. Cell Biol. 10: 1498.
19. Hassanain, et al., 1993. Anal. Biochem. 213: 162.
20. Singh, et al., 1988. Cell 52:415.
21. Singh, et al., (1995) J. Biol. Chem. 270, 10631–10639.
22. Reddy, et al., (1994) J. Biol. Chem., 269, 25369–25372
23. Chaturvedi et al., (1994). J. Biol. Chem. 269:14575–14583.
24. Huang, et al., (1991) Proc. Natl. Acad. Sci. USA, 88, 5292–5296.
25. Finco et al., (1994). Proc. Natl. Acad. Sci. USA 91, 11884–11888.
26. Thanos, D. and Maniatis, T (1995) Cell, 80, 529–532.
27. Huang, et al., (1988) Cancer Res. 48, 5941–5946.
28. Huang, et al., (1992) Carcinogenesis 13, 2183–2186.
29. Takada, et al., (1994) Cancer Res. 54, 4653–4659.
30. Ammon et al., (1993) J. Ethnopharmacol. 38, 113–119
31. Kumar, et al., 1992, Mol. Cell. Biol. 12, 3094–3106.
32. Dressler, et al., (1992) Science, 255, 1715–1718.
33. Schutze, et al. Cell, 71, 765–76.
34. Mathias, et al., (1991) J. Biol. Chem. 266. 10009–10013.
35. Yang, et al., (1993) J. Biol. Chem. 268, 20520–20523.
36. Schulze-Osthoff, et al., (1993) EMBO J. 12, 3095–3104.
37. Devary, et al., (1993) Science 261, 1442–1445.
38. Geng, et al., J. Immunol. 151, 6692–6700.
39. Koong, et al., (1994) Cancer Res. 54, 1425–1430.
40. Eicher, et al., (1994) J. Immunol. 152, 2710–2719.
41. Schreck, et al., (1992) J. Exp. Med. 175, 1181–1194.
42. Schreck, et al., (1991) EMBO J. 10, 2247–2258.
43. Schievien, et al., (1993) Blood 82, 1212–1220.
44. Reddy, S. and Aggarwal, B. B. (1994) FEBS Lett. 341, 19–22.
45. Brouet, et al., (1995) BBRC 206, 533–540
46. Oshima, H. and Bartsch, H. (1994) Mutat. Res. 305, 253–264.
47. Halliwell, B. (1994) The Lancet 344, 721–724.
48. Kim, et al., (1995) J. Immunol. 154, 4741–4748.
49. Meyer, et al., (1993) EMBO J. 12, 2005–2015.
50. Meichle, et al., (1990) J. Biol. Chem. 265, 8339–8343.
51. Yanaga, F., and Watson, S. P. (1993) Biochem. J. 298, 733–738.

52. Mahon et al., (1995) Biochemical Soc. Trans. 23, p111S.

What is claimed is:

1. A method of inhibiting the activation of the NFκB transcription factor in treating a human for a pathophysiological state selected from the group consisting of toxic/septic shock and graft vs host reaction comprising the step of administering to said human a pharmacologically effective dose of curcumin.

2. The method of claim 1, wherein said curcumin is administered in a dose of from about 1 mg/kg to about 100 mg/kg.

* * * * *

UNITED STATES PATENT AND TRADEMARK OFFICE
CERTIFICATE OF CORRECTION

PATENT NO. : 5,891,924
DATED : April 6, 1999
INVENTOR(S) : Bharat B. Aggarwal

It is certified that error appears in the above-indentified patent and that said Letters Patent is hereby corrected as shown below:

In Column 1, line 31, "a n" should read --an--.

In Column 1, line 33, "b y" should read --by--.

In Column 5, lines 37, where the sequence reads "GCCAC..." should read --GCTCAC...--.

In Column 8, line 17, "degrdation" should read --degradation--.

In Column 8, line 43, "s erine/" should read --serine/--.

Signed and Sealed this

Twentieth Day of March, 2001

*Attest:*

NICHOLAS P. GODICI

*Attesting Officer*   *Acting Director of the United States Patent and Trademark Office*